United States Patent
Enomoto et al.

(10) Patent No.: US 10,172,583 B2
(45) Date of Patent: Jan. 8, 2019

(54) RADIOGRAPHY APPARATUS, RADIOGRAPHY METHOD, AND RADIOGRAPHY PROGRAM

(71) Applicant: FUJIFILM CORPORATION, Minato-ku, Tokyo (JP)

(72) Inventors: Jun Enomoto, Kanagawa (JP); Noriaki Ida, Kanagawa (JP); Daiki Harada, Kanagawa (JP); Takahiro Kawamura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 253 days.

(21) Appl. No.: 15/239,844

(22) Filed: Aug. 18, 2016

(65) Prior Publication Data

US 2016/0354051 A1  Dec. 8, 2016

Related U.S. Application Data

(63) Continuation of application No. PCT/JP2015/060002, filed on Mar. 30, 2015.

(30) Foreign Application Priority Data

Mar. 28, 2014 (JP) .................... 2014-070545
Sep. 25, 2014 (JP) .................... 2014-195704

(51) Int. Cl.
*A61B 6/00* (2006.01)

(52) U.S. Cl.
CPC .......... *A61B 6/5282* (2013.01); *A61B 6/4241* (2013.01); *A61B 6/461* (2013.01)

(58) Field of Classification Search
CPC ... A61B 6/4283; A61B 6/4291; A61B 6/4405; A61B 6/461; A61B 6/467; A61B 6/5282; A61B 6/563
See application file for complete search history.

(56) References Cited

U.S. PATENT DOCUMENTS

2004/0101093 A1* 5/2004 Matsumoto ............ A61B 6/032
378/22
2004/0228439 A1* 11/2004 Tsujii ....................... A61B 6/06
378/62

(Continued)

FOREIGN PATENT DOCUMENTS

| JP | H05/82111 | B2 | 11/1993 |
| JP | H10-262961 | A | 10/1998 |
| JP | 2004-329783 | A | 11/2004 |
| JP | 2013-172881 | A | 9/2013 |
| JP | 2014207958 | A * | 11/2014 | ............ A61B 6/5282 |
| WO | WO 2014156545 | A1 * | 10/2014 | ............ A61B 6/5282 |

*Primary Examiner* — Chih-Cheng Kao
(74) *Attorney, Agent, or Firm* — SOLARIS Intellectual Property Group, PLLC

(57) ABSTRACT

A derivation unit acquires imaging conditions corresponding to order information received by a receiving unit based on a table stored in a storage unit and sets the imaging conditions in a radiation source control unit. The radiation source control unit controls a radiation source based on the set imaging conditions such that a radiographic image is captured. An acquisition unit acquires the actual values of the imaging conditions from the radiation source control unit. The derivation unit derives virtual grid characteristics based on the actual values of the imaging conditions. An execution unit acquires a captured radiographic image through a detector control unit. The execution unit performs a virtual grid process for the acquired radiographic image based on the virtual grid characteristics derived by the derivation unit and the acquired imaging conditions to generate a radiographic image from which the influence of scattered radiation has been removed.

10 Claims, 10 Drawing Sheets

(56) References Cited

U.S. PATENT DOCUMENTS

| | | | |
|---|---|---|---|
| 2010/0046822 A1* | 2/2010 | Li | A61B 6/5282 382/132 |
| 2013/0259352 A1* | 10/2013 | Wang | A61B 6/50 382/132 |
| 2015/0251018 A1* | 9/2015 | Tajima | A61B 6/5282 378/28 |
| 2015/0379711 A1* | 12/2015 | Imai | A61B 6/5282 382/132 |

* cited by examiner

FIG. 2

| | SUBJECT INFORMATION | | | IMAGING CONDITIONS | | | GRID CHARACTERISTICS |
|---|---|---|---|---|---|---|---|
| | AGE | BODY TYPE | PART TO BE IMAGED | TUBE VOLTAGE | TUBE CURRENT | IRRADIATION TIME | GRID RATIO |
| (EXAMPLE 1) | ADULT | NORMAL BODY TYPE | CHEST | $\alpha$ kVp | $\beta$ mA | $\gamma$ msec | 3:1 |
| (EXAMPLE 2) | ADULT | FAT BODY TYPE | CHEST | $\alpha+\theta$ kVp | $\beta$ mA | $\gamma$ msec | 4:1 |

# RADIOGRAPHY APPARATUS, RADIOGRAPHY METHOD, AND RADIOGRAPHY PROGRAM

CROSS-REFERENCE TO RELATED APPLICATIONS

This application is a continuation application of International Application No. PCT/JP2015/060002, filed on Mar. 30, 2015, which is incorporated herein by reference in its entirety. Further, this application claims priority from Japanese Patent Application No. 2014-070545, filed on Mar. 28, 2014, and Japanese Patent Application No. 2014-195704, filed on Sep. 25, 2014, the disclosures of which are incorporated by reference herein in their entireties.

BACKGROUND

Technical Field

The present invention relates to a radiography apparatus, a radiography method, and a radiography program.

Related Art

In the related art, in a case in which a radiographic image of a subject is captured using radiation that is transmitted through the subject, particularly, in a case in which the thickness of the subject is large, the radiation is scattered in the subject and the scattered radiation (hereinafter, also referred to a "scattered ray") causes a reduction in the contrast of the captured radiographic image. For this reason, in some cases, a scattered radiation removal grid (hereinafter, simply referred to as a grid) is provided between a subject and a radiation detector in order to reduce the influence of scattered radiation in the capture of a radiographic image. When imaging is performed using the grid, radiation which is scattered by the subject is less likely to reach the radiation detector. Therefore, it is possible to improve the contrast of the radiographic image (for example, see Japanese Patent Application Publication (JP-B) No. H05-82111, Japanese Patent Application Laid-Open (JP-A) No. 10-262961, and JP-A No. 2004-329783).

In a case in which a radiographic image is captured using a grid process, a grid with appropriate characteristics is used according to, for example, imaging conditions. Therefore, in some cases, when the characteristics of the grid used are set, the burden of the setting operation on a user, such as a technician or a doctor, increases.

However, when imaging is performed using the grid as in the related art, a subject image and a fine stripe pattern (moire) corresponding to a grid pitch are included in a radiographic image, which makes it difficult to see a captured radiographic image. Image processing for removing the stripe pattern is also known (for example, see JP-A No. 2013-172881). In some cases, the processing time increases.

There is a technique that performs image processing for a radiographic image which has been captured, without providing a grid between the subject and a radiation detector, to remove the influence of scattered radiation. In addition, the characteristics of the grid that is assumed to be used can be designated and the amount of removal of scattered radiation can be controlled. Hereinafter, a process that performs image processing on the basis of the characteristics of a grid, which is assumed to be used, to remove the influence of scattered radiation to the same extent as that in a case in which a grid is provided is referred to as a virtual grid process.

In a case in which imaging is performed using the virtual grid process, appropriate characteristics of a virtual grid that is assumed to be used are set according to, for example, the imaging conditions, similarly to a case in which imaging is performed using a grid. Therefore, the burden of a setting operation on the user increases.

SUMMARY

The invention provides a radiography apparatus, a radiography method, and a radiography program that can reduce the burden of an operation related to the setting of imaging conditions on a user.

According to a first aspect of the invention, there is provided a radiography apparatus that performs a scattered radiation removal process of removing an influence of scattered radiation included in radiation which has passed through a subject for a radiographic image captured by irradiating the subject with the radiation. The radiography apparatus includes: an acquisition unit that acquires imaging conditions of the radiographic image; a derivation unit that derives virtual grid characteristics which are characteristics of a grid virtually used to remove the scattered radiation in the capture of the radiographic image and are used to set an amount of removal of the scattered radiation, on the basis of the imaging conditions acquired by the acquisition unit; and an execution unit that performs the scattered radiation removal process for the radiographic image with the amount of removal corresponding to the virtual grid characteristics derived by the derivation unit.

According to a second aspect of the invention, the radiography apparatus according to the first aspect may further include a storage unit that stores the imaging conditions and the virtual grid characteristics corresponding to the imaging conditions so as to be associated with each other. The derivation unit may read the virtual grid characteristics corresponding to the imaging conditions acquired by the acquisition unit from the storage unit and derive the virtual grid characteristics.

According to a third aspect of the invention, in the first aspect or the second aspect, the derivation unit may derive the virtual grid characteristics, using information related to a physique of the subject, in addition to the acquired imaging conditions.

According to a fourth aspect of the invention, in any one of the first to third aspects, the virtual grid characteristics may be a grid ratio.

According to a fifth aspect of the invention, in any one of the first to fourth aspects, the acquisition unit may acquire actual values of the imaging conditions.

According to a sixth aspect of the invention, in any one of the first to fifth aspects, the derivation unit may derive the virtual grid characteristics on the basis of an estimated value of a body thickness of the subject.

According to a seventh aspect of the invention, in any one of the first to sixth aspects, the radiography apparatus may irradiate the subject with radiations having different energy levels to capture a first radiographic image and a second radiographic image. The derivation unit may derive virtual grid characteristics for each of the first radiographic image and the second radiographic image. The execution unit may perform the scattered radiation removal process for each of the first radiographic image and the second radiographic image. The radiography apparatus may further include an energy subtraction processing unit that matches pixels of the first radiographic image and the second radiographic image subjected to the scattered radiation removal process by the execution unit and performs a weighted difference calculation process to generate a difference image.

According to an eighth aspect of the invention, in the seventh aspect, the virtual grid characteristics may be a grid ratio and the grid ratio may become higher as the energy level of the radiation emitted to the subject becomes higher.

According to a ninth aspect of the invention, there is provided a radiography method that performs a scattered radiation removal process of removing an influence of scattered radiation included in radiation which has passed through a subject for a radiographic image captured by irradiating the subject with the radiation. The radiography method includes: acquiring imaging conditions of the radiographic image; deriving virtual grid characteristics which are characteristics of a grid virtually used to remove the scattered radiation in the capture of the radiographic image and are used to set an amount of removal of the scattered radiation, on the basis of the acquired imaging conditions; and performing the scattered radiation removal process for the radiographic image with the amount of removal corresponding to the derived virtual grid characteristics.

According to a tenth aspect of the invention, there is provided a radiography program that causes a computer to perform a radiography method which performs a scattered radiation removal process of removing an influence of scattered radiation included in radiation which has passed through a subject for a radiographic image captured by irradiating the subject with the radiation. The radiography program causes the computer to perform: acquiring imaging conditions of the radiographic image; deriving virtual grid characteristics which are characteristics of a grid virtually used to remove the scattered radiation in the capture of the radiographic image and are used to set an amount of removal of the scattered radiation, on the basis of the acquired imaging conditions; and performing the scattered radiation removal process for the radiographic image with the amount of removal corresponding to the derived virtual grid characteristics.

The invention provides a radiography apparatus, a radiography method, and a radiography program that can reduce the burden of an operation related to the setting of imaging conditions on a user.

BRIEF DESCRIPTION OF THE DRAWINGS

FIG. 2 is a diagram illustrating an example of a table indicating a correspondence relationship between virtual grid characteristics, subject information, and imaging conditions.

DESCRIPTION OF EMBODIMENTS

Hereinafter, embodiments of the invention will be described in detail with reference to the drawings. These embodiments do not limit the invention.

First Embodiment

A radiography apparatus according to this embodiment does not have a grid that is provided between a radiation detector and a subject and has a function that performs a virtual grid process of performing image processing for a captured radiographic image to remove the influence of a scattered radiation.

Figure 1:
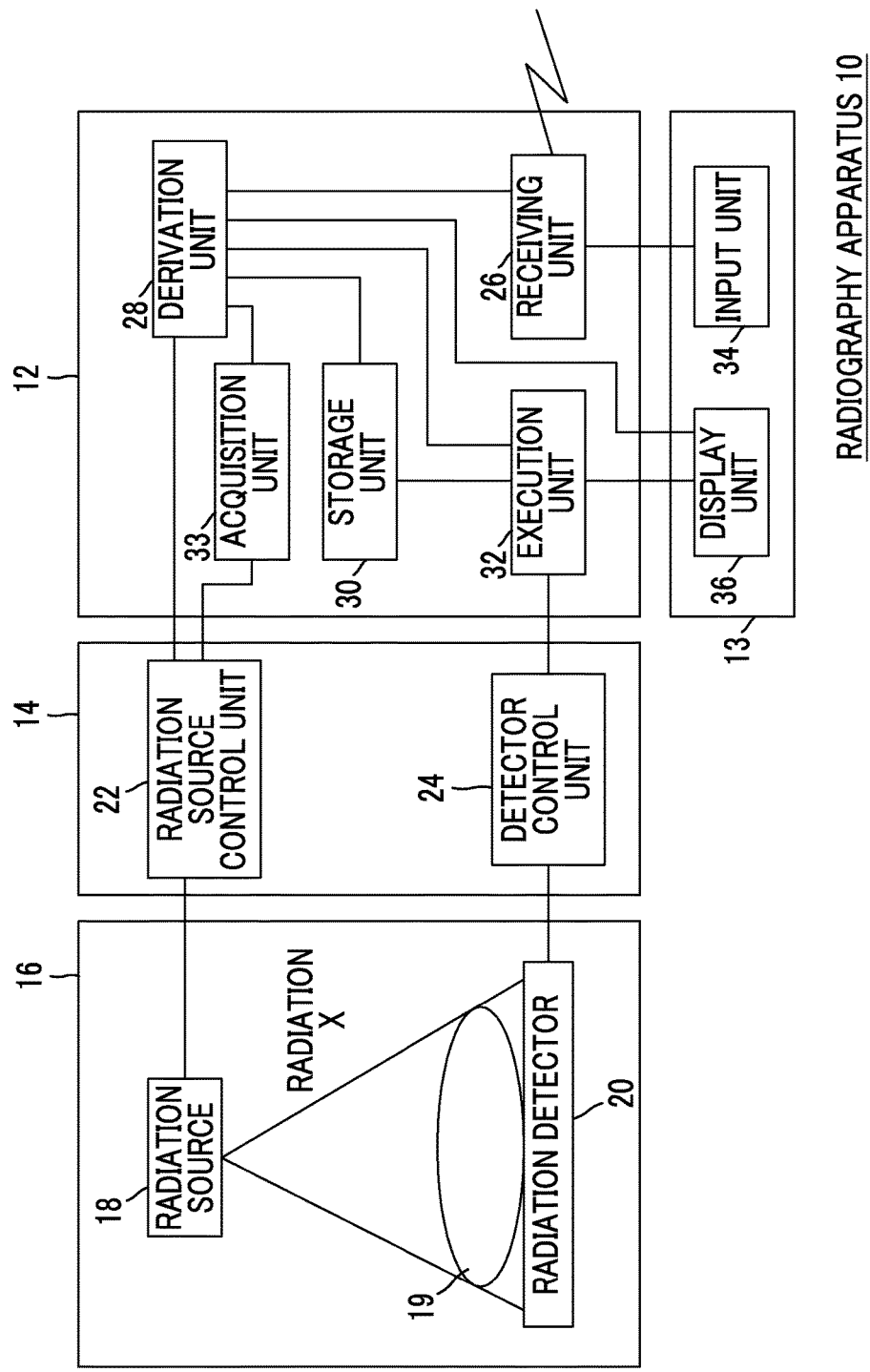
FIG. 1 is a diagram illustrating an example of the structure a radiography apparatus according to a first embodiment.

First, the structure of the radiography apparatus according to this embodiment will be described. FIG. 1 illustrates an example of the structure of the radiography apparatus according to this embodiment. As illustrated in FIG. 1, a radiography apparatus 10 according to this embodiment includes an image processing device 12, a user interface (U/I) unit 13, a control device 14, and an imaging device 16.

The imaging device 16 includes a radiation source 18 and a radiation detector 20. The radiation source 18 has a function of irradiating a subject 19 with radiation X under the control of a radiation source control unit 22. The radiation detector 20 has a function that detects the radiation X which has been emitted from the radiation source 18 and then passed through the subject 19 and outputs a radiographic image of the subject 19. The radiation detector 20 according to this embodiment is a portable electronic cassette and is a so-called flat panel detector (FPD).

The control device 14 includes the radiation source control unit 22 and a detector control unit 24. The radiation source control unit 22 has a function of controlling the driving of the radiation source 18 according to imaging conditions set by the image processing device 12. The detector control unit 24 has a function that controls the radiation detector 20, acquires a radiographic image output from the radiation detector 20, and outputs the radiographic image to the image processing device 12.

The image processing device 12 includes a receiving unit 26, a derivation unit 28, a storage unit 30, an execution unit 32, and an acquisition unit 33. The U/I unit 13 includes an input unit 34 and a display unit 36. A console related to the capture of a radiographic image is given as an example of the apparatus including the image processing device 12, the U/I unit 13, and the control device 14 (which will be described below; see FIG. 10).

The input unit 34 is used by a user to input an instruction related to the capture of a radiographic image to the image processing device 12. Examples of the input unit 34 include a keyboard, a mouse, and a touch panel.

The receiving unit 26 has a function of receiving the user's instruction to capture a radiographic image from the input unit 34 of the U/I unit 13. In this embodiment, a person who operates the radiography apparatus 10 or a person who performs radiography, such as a radiological technician or a doctor, is referred to as a "user".

Therefore, the U/I unit 13 has a function of detecting an instruction (operation) which is input by the user through the input unit 34.

The receiving unit 26 according to this embodiment has a function of acquiring information, such as an order related to the capture of a radiographic image, from an external system, such as a radiology information system (RIS), through a communication line or a network, such as a local area network (LAN). Therefore, the U/I unit 13 has a network interface (I/F) function.

The storage unit 30 has a function of storing a table indicating the correspondence relationship among the information of the subject 19, imaging conditions, and virtual grid characteristics. In addition, the storage unit 30 according to this embodiment has a function of storing a table in which the virtual grid characteristics are associated with information required for the execution unit 32 to perform the virtual grid process. The information for performing the virtual grid process includes scattered radiation transmittance Ts for the virtual grid and primary radiation transmittance Tp which is the transmittance of primary radiation that passes through the subject 19 and is directly emitted to the radiation detector 20. The values of the scattered radiation transmittance Ts and the primary radiation transmittance Tp are equal to or greater than 0 and equal to or less than 1. The virtual grid characteristics are not limited to this embodiment. For example, the virtual grid characteristics may include grid density (lattice density), information indicating whether the grid is a convergence type or a parallel type, a focusing distance in a case in which the grid is a convergence type, and an interspace material.

The storage unit 30 is preferably a non-volatile storage unit and is, for example, a hard disk drive (HDD). FIG. 2 illustrates an example of the table indicating the correspondence relationship among the subject information, the imaging conditions, and the virtual grid characteristics.

As illustrated in FIG. 2, the subject information which is an example of information related to the physique of the subject in the disclosed technique according to this embodiment is mainly information related to the physique of the subject 19 and includes, for example, age, a body type, and a part to be imaged. The amount of scattered radiation X varies depending on the body type (for example, a normal body type or a fat body type). For example, in the case of the fat body type, that is, when the thickness of the subject 19 (thickness in an irradiation direction) is large, the amount of scattered radiation is large. In addition, the distribution of scattered radiation varies depending on the part (for example, the chest or the abdomen) to be imaged. The physique (body type) of the subject 19 may be estimated from the height and weight of the subject 19. In addition, the subject information may include information related to the position of the subject 19 on a radiographic image and the distribution of the composition of the subject 19.

In this embodiment, a tube voltage of the radiation source 18 and the amount of radiation X emitted to the subject 19 (tube current x irradiation time) are used as the imaging conditions. The imaging conditions are not limited thereto and may include, for example, the distance from the radiation source 18 to the radiation detector 20 and the distance from the subject 19 to the radiation detector 20.

The virtual grid characteristics are the characteristics of a virtual grid that is assumed to be used in order to perform a virtual grid process which performs image processing for a captured radiographic image to remove the influence of scattered radiation.

In the radiography apparatus 10 according to this embodiment, a grid ratio is used as the virtual grid characteristics. In general, the grid has a structure in which thin lead films having a high absorbance of radiation X and a material (interspace material) which is interposed between the thin lead films and has a low absorbance of radiation X are alternately arranged at a fine grid density of, for example, about 4.0 lines/mm. For example, aluminum, paper, and carbon fiber are used as the interspace material. The grid ratio is defined by the ratio of the heights of the lead films in a case in which the distance between the lead films (the thickness of the interspace material) is "1". When the grid ratio is high, the amount of scattered radiation is effectively reduced. In general, as the tube voltage of the radiation source 18 used becomes higher (the energy of the radiation X becomes higher), a higher grid ratio is used.

The acquisition unit 33 has a function of acquiring imaging conditions. In a case in which a radiographic image is captured, in the image processing device 12 according to this embodiment, the acquisition unit 33 acquires the actual values of the imaging conditions under which radiation is actually emitted to the subject 19. In the actual imaging process, in some cases, the imaging conditions set by the radiation source control unit 22 are different from the actual values of the imaging conditions. For example, in a case in which the amount of radiation that is more or less than that set by the radiation source control unit 22 is emitted to the subject 19 due to the deterioration of a bulb of the radiation source 18 or in a case in which the body thickness of the subject 19 is large, the user who performs imaging adjusts the set imaging conditions. In some cases, the adjustment causes the set imaging conditions to be different from the actual value. The method of the acquisition unit 33 acquiring the actual values of the imaging conditions is not particularly limited. For example, the radiation source control unit 22 may monitor, for example, the radiation source 18 and acquire the tube voltage or the tube current of the radiation source 18 during the emission of the radiation X and the acquisition unit 33 may acquire the actual values of the imaging conditions through the radiation source control unit 22.

The derivation unit 28 has a function of deriving the virtual grid characteristics (grid ratio) corresponding to the imaging conditions acquired by the acquisition unit 33 on the basis of the table indicating the correspondence relationship which is stored in the storage unit 30. In addition, the derivation unit 28 has a function of setting the imaging conditions in the control device 14 (radiation source control unit 22). Furthermore, the derivation unit 28 has a function of displaying information related to the derived virtual grid characteristics (grid ratio) on the display unit 36.

The execution unit 32 has a function that acquires the radiographic image captured by the imaging device 16, specifically, the radiographic image output from the radiation detector 20 through the detector control unit 24 and performs the virtual grid process for the acquired radiographic image. The radiographic image that has been subjected to the virtual grid process by the execution unit 32 is displayed on the display unit 36 of the U/I unit 13. The display unit 36 has a function of displaying, for example, information related the capture of a radiographic image and a captured radiographic image. A display, such as a liquid crystal display, is given as an example of the display unit 36.

An example of the virtual grid process which is performed by the execution unit 32 to remove scattered radiation will be described.

The execution unit 32 analyzes the radiographic image which is acquired from the radiation detector 20 through the detector control unit 24 and obtains scattered component information, that is, a scattered radiation content distribution. The execution unit 32 according to this embodiment analyzes the radiographic image on the basis of irradiation field information, the subject information, and the imaging conditions when the radiographic image is captured. The irradiation field information is information indicating an irradiation field distribution related to the position and size of the irradiation field which is included in the radiographic image in a case in which imaging is performed using an irradiation field diaphragm.

As described above, the irradiation field information, the subject information, and the imaging conditions are factors for determining the distribution of the scattered radiation included in the radiographic image. For example, the amount of scattered radiation varies depending on the size of the irradiation field. As the body thickness of the subject 19 increases, the amount of scattered radiation increases. If there is air between the subject 19 and the radiation detector 20, the amount of scattered radiation decreases. Therefore, the execution unit 32 can accurately acquire the scattered radiation content distribution, using the information.

The execution unit 32 calculates a primary radiation image and a scattered radiation image from the body thickness distribution $T(x, y)$ of the subject 19 in the radiographic image, on the basis of the following Expressions (1) and (2). In addition, the execution unit 32 calculates a scattered radiation content distribution $S(x, y)$ from the calculated primary radiation image and scattered radiation image, on the basis of the following Expression (3). The scattered radiation content distribution $S(x, y)$ has a value of 0 to 1.

$$Ip(x, y)=Io(x, y)\times\exp(-\mu\times T(x, y)) \quad (1)$$

$$Is(x, y)=Io(x, y)*S\sigma(T(x, y)) \quad (2)$$

$$S(x, y)=Is(x, y)/(Is(x, y)+Ip(x, y)) \quad (3)$$

In Expressions (1) to (3), $(x, y)$ is the coordinates of a pixel position in a radiographic image, $Ip(x, y)$ is a primary radiation image at the pixel position $(x, y)$, and $Is(x, y)$ is a scattered radiation image at the pixel position $(x, y)$. In addition, $Io(x, y)$ is an incident dose on the surface of the subject 19 at the pixel position $(x, y)$. Furthermore, $\mu$ is a linear attenuation coefficient of the subject and $S\sigma(T(x, y))$ is a convolution kernel indicating scattering characteristics corresponding to the body thickness of the subject 19 at the pixel position $(x, y)$. Expression (1) is based on a known exponential attenuation rule and Expression (2) is based on the method described in "J. M. Boon et al., An analytical model of the scattered radiation distribution in diagnostic radiolog, Med. Phys. 15(5), September/October 1988" (Reference Document 1). Even if the incident dose $Io(x, y)$ on the surface of the subject 19 is defined as any value, the incident dose $Io(x, y)$ is cancelled by division when $S(x, y)$ is calculated. Therefore, the incident dose $Io(x, y)$ may be set to an arbitrary value, for example, "1".

The body thickness distribution $T(x, y)$ of the subject 19 may be calculated by converting the pixel value of the radiographic image into a thickness, using the linear attenuation coefficient, on the assumption that a brightness distribution in the radiographic image is substantially identical to the body thickness distribution of the subject 19. Alternatively, the body thickness of the subject 19 may be measured using, for example, a sensor or may be approximated by a model, such as a cube or an elliptic cylinder.

In Expression (2), "*" is an operator indicating a convolution operation. The properties of a kernel change depending on, for example, the distribution of the irradiation field, the distribution of the composition of the subject 19, the imaging conditions, and the characteristics of the radiation detector 20, in addition to the body thickness of the subject 19. According to the method described in Reference Document 1, scattered radiation can be approximated by the convolution of a point spread function ($S\sigma(T(x, y))$ in Expression (2)) with respect to the primary radiation. In addition, $S\sigma(T(x, y))$ can be experimentally calculated on the basis of, for example, the irradiation field information, the subject information, the imaging conditions.

In addition, $S\sigma(T(x, y))$ may be calculated on the basis of the irradiation field information, the subject information, and the imaging conditions during imaging, or may be calculated using a table indicating the correspondence relationship between $S\sigma(T(x, y))$ and various kinds of irradiation field information, various kinds of subject information, and various imaging conditions. In this case, the table indicating the correspondence relationship may be stored in the storage unit 30 in advance and $S\sigma(T(x, y))$ may be calculated on the basis of the irradiation field information, the subject information, and the imaging conditions during imaging, with reference to the table indicating the correspondence relationship which is stored in the storage unit 30. In addition, $S\sigma(T(x, y))$ may be approximated by $T(x, y)$.

The execution unit 32 performs the scattered radiation removal process by reducing a frequency component in a frequency band which is regarded as scattered radiation in the radiographic image, on the basis of the virtual grid characteristics and the scattered component information. The execution unit 32 performs frequency decomposition for the radiographic image to acquire frequency components for each of plural frequency bands and reduces the gain of at least one frequency component. Then, the execution unit 32 synthesizes the processed frequency component and the other frequency components to acquire a radiographic image subjected to the scattered radiation removal process. As a frequency decomposition method, in addition to a method for performing multi-resolution conversion for the radiographic image, other known methods, such as wavelet transform and Fourier transform, can be used.

The execution unit 32 calculates a conversion coefficient $R(x, y)$ for converting a frequency component from the scattered radiation transmittance Ts, the primary radiation transmittance Tp, and the scattered radiation content distribution $S(x, y)$, using the following Expression (4).

$$R(x, y)=S(x, y)\times Ts+(1-S(x, y))\times Tp \quad (4)$$

Since each of the scattered radiation transmittance Ts, the primary radiation transmittance Tp, and the scattered radiation content distribution $S(x, y)$ has a value that is equal to or greater than 0 and equal to or less than 1, the conversion coefficient $R(x, y)$ also has a value that is equal to or greater than 0 and equal to or less than 1. The execution unit 32 calculates the conversion coefficient $R(x, y)$ for each of plural frequency bands.

In the following description, the pixel value of a radiographic image is represented by $I(x, y)$, a frequency component image obtained by frequency decomposition is represented by $I(x, y, r)$, frequency synthesis is represented by $I(x, y)=\Sigma r I(x, y, r)$, a conversion coefficient for each frequency band is represented by $R(x, y, r)$, and the scattered radiation transmittance and the primary radiation transmittance for each frequency band are represented by $Ts(r)$ and $Tp(r)$, respectively. In addition, "r" indicates a layer of a frequency band. As r becomes greater, the frequency becomes lower. Therefore, $I(x, y, r)$ indicates a frequency component image of a certain frequency band. The scattered radiation content distribution $S(x, y)$ for the radiographic image may be used without any change, or the scattered radiation content distribution S(x, y) may be acquired for each frequency band, similarly to the scattered radiation transmittance Ts and the primary radiation transmittance Tp.

In this embodiment, the execution unit 32 calculates a conversion coefficient R(x, y, r) for each frequency component and multiplies the frequency component image I(x, y, r) by the conversion coefficient R(x, y, r) of a corresponding frequency band to convert the pixel value of the frequency component image I(x, y, r). Then, the execution unit 32 performs frequency synthesis for the frequency component image I(x, y, r) multiplied by the conversion coefficient R(x, y, r) (that is, I(x, y, r)×R(x, y, r)) to acquire a processed radiographic image I'(x, y). Therefore, the process which is performed by the execution unit 32 is represented by the following Expression (5). Since the conversion coefficient R(x, y, r) has a value that is equal to or greater than 0 and equal to or less than 1, the pixel value of the frequency component at the pixel position (x, y), that is, the gain is reduced by multiplying the frequency component (x, y, r) by the conversion coefficient R(x, y, r) of the corresponding frequency band.

$$I'(x, y) = \sum r\{I(x, y, r) \times R(x, y, r)\}$$
$$= \sum r\{I(x, y, r) \times (S(x, y) \times Ts(r) + (1 - S(x, y)) \times Tp(r))\} \quad (5)$$

In the execution unit 32, a scattered radiation component is removed according to the characteristics (type) of the grid that is assumed to be used, in the processed radiographic image acquired by performing the process illustrated in Expression (5) using the conversion coefficient calculated by the above-mentioned method.

The image processing device 12 according to this embodiment is implemented by, for example, a computer including a central processing unit (CPU), a read only memory (ROM), a random access memory (RAM), and an HDD. For example, the CPU executes an imaging control process program, which will be described in detail below, to implement the functions of the receiving unit 26, the derivation unit 28, the execution unit 21, and the acquisition unit 33. In addition, the imaging control process program may be stored in a non-volatile storage unit, such as a ROM, in advance or may be installed in the image processing device 12 through a portable storage unit, such as a universal serial bus (USB) memory, or a line, such as a network.

Next, the imaging control process performed by the image processing device 12 of the radiography apparatus 10 according to this embodiment will be described. The imaging control process corresponds to an example of a radiography method which is a disclosed technique.

Figure 3:
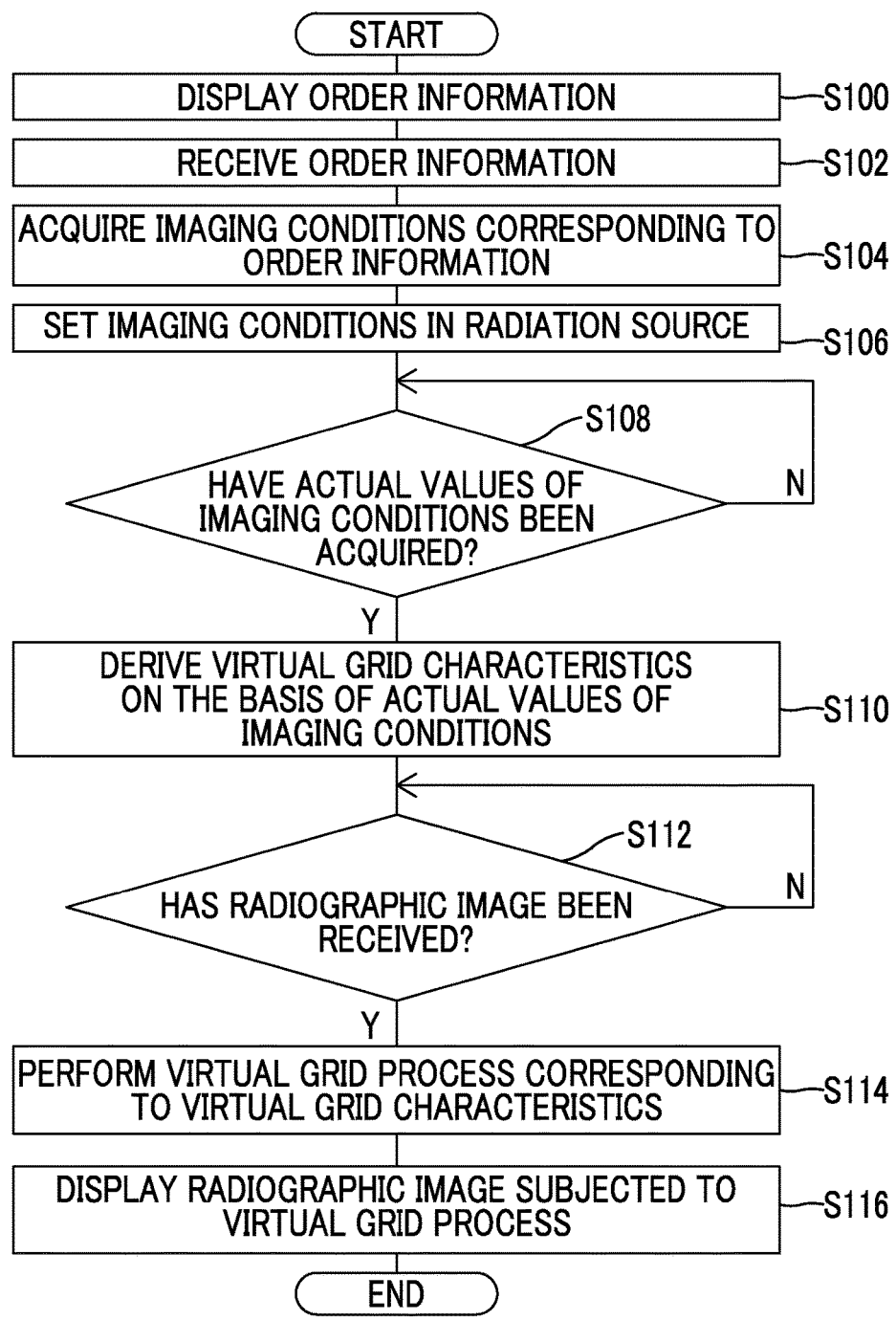
FIG. 3 is a flowchart illustrating an example of an imaging control process according to the first embodiment.

FIG. 3 is a flowchart illustrating an example of the imaging control process according to this embodiment. The imaging control process illustrated in FIG. 3 is performed, for example, in a case in which the receiving unit 26 receives an instruction to capture a radiographic image.

In Step S100, the receiving unit 26 displays order information which is related to the capture of a radiographic image and is received from an external system or the input unit 34 on the display unit 36. Here, examples of the displayed order information include the name or identification (ID) of the subject 19 for identifying the subject 19, the part to be imaged, an imaging direction (for example, the front side), and the number of images to be captured. However, the order information is not particularly limited.

The order information may be any information for specifying the capture of a radiographic image which will be performed.

The user sets the radiation detector 20 and the radiation source 18 at an imaging position, with the subject 19 interposed therebetween, on the basis of the order information displayed on the display unit 36. In addition, the user inputs the order information on the basis of the order information displayed on the display unit 36. However, the invention is not limited to this embodiment. The display of the order information in Step S100 may be omitted and the user may input all of the order information through the input unit 34.

Then, in Step S102, the receiving unit 26 receives the order information which has been input by the user through the input unit 34 on the basis of the displayed order information. The received information may be sequentially displayed on the display unit 36 to prompt the user to check the received information.

Then, in Step S104, the derivation unit 28 acquires the imaging conditions corresponding to the received order information, on the basis of, for example, the table stored in the storage unit 30 illustrated in FIG. 2. For example, in a case in which subject information is received as the order information, the derivation unit 28 acquires the imaging conditions corresponding to the received subject information. In Example 1 illustrated in FIG. 2, for the subject information in which age is an adult, the body type is a normal body type, and the part to be imaged is the chest, the following imaging conditions are acquired: a tube voltage of α kVp; a tube current of β mA; and an irradiation time of γ msec. In a case in which the imaging conditions are acquired, the subject information, particularly, the physique (for example, the body type) of the subject 19 may also be considered. As described above, in a case in which the body thickness of the subject 19 is large, it is preferable that the tube voltage of the radiation source 18 is higher than that in a case in which the body thickness is small or in a general case. Therefore, it is preferable to use a table in which imaging conditions that are different from the general (in a case of a general body thickness) imaging conditions (mainly the tube voltage) are associated with the subject information, particularly, the body thickness of the subject 19. For example, in Example 2 illustrated in FIG. 2, unlike Example 1, since the body type is a "fat body type", the tube voltage, which is the imaging conditions, is α+θ(θ>0) kVp and is higher than that in Example 1.

In the image processing device 12 according to this embodiment, the derivation unit 28 acquires the imaging conditions from the order information such as the subject information. However, the user may input the imaging conditions through the input unit 34.

Then, in Step S106, the derivation unit 28 sets the acquired imaging conditions in the radiation source control unit 22 of the control device 14. The radiation source control unit 22 controls the radiation source 18 on the basis of the imaging conditions set by the derivation unit 28 such that a radiographic image is captured.

When the imaging conditions are set, the radiation source control unit 22 controls the radiation source 18 such that the subject 19 is irradiated with the radiation X. The detector control unit 24 controls the radiation detector 20 such that the radiation detector 20 detects the radiation X transmitted through the subject 19 and outputs a radiographic image indicating an image of the subject 19 to the detector control unit 24.

Then, in Step S108, the acquisition unit 33 determines whether the actual values of the imaging conditions have been acquired. In a case in which the actual values have not been acquired, the image processing device 12 is in a standby state. On the other hand, in a case in which the actual values of the imaging conditions have been acquired, the process proceeds to Step S110.

Then, in Step S110, the derivation unit 28 derives the virtual grid characteristics (grid ratio) corresponding to the actual values of the imaging conditions acquired by the acquisition unit 33, on the basis of the table stored in the storage unit 30. As illustrated in Example 2 of FIG. 2, in a case in which a tube voltage of $\alpha+\theta$ kVp, a tube current of $\beta$ mA, and an irradiation time of $\gamma$ msec are acquired as the actual values of the imaging conditions, the derivation unit 28 derives a virtual grid characteristic (grid characteristic) of 4:1. The derivation unit 28 may derive the virtual grid characteristics, considering the physique of the subject 19. For example, in a case in which the body type is a normal type and the tube voltage is 70 kVp, it is preferable that the grid ratio is 4:1. In a case in which the body type is a fat type and the tube voltage is 70 kVp, the amount of radiation that reaches the radiation detector 20 is less than that in a case in which the body type is a normal type. Therefore, it is preferable that the grid ratio is 3:1. In this case, since the body type of the subject 19 is considered, it is possible to derive a more appropriate grid ratio than that in a case in which the grid ratio is derived on the basis of information related to a tube voltage of 70 kVp, without using information related to the physique (body type).

Then, in Step S112, the execution unit 32 determines whether a radiographic image has been received from the radiation detector 20 through the detector control unit 24. In a case in which a radiographic image has not been received, for example, in a case in which a radiographic image is being captured, the execution unit 32 is in a standby state. On the other hand, when a radiographic image has been received, the process proceeds to Step S114.

In Step S114, the execution unit 32 performs the virtual grid process corresponding to the virtual grid characteristics derived by the derivation unit 28 in Step S110 for the received radiographic image to remove the influence of scattered radiation from the radiographic image. Specifically, the execution unit 32 acquires the scattered radiation transmittance Ts and the primary radiation transmittance Tp corresponding to the derived virtual grid characteristics (grid ratio) from the table indicating the correspondence relationship which is stored in the storage unit 30. In addition, the execution unit 32 acquires the actual values of the imaging conditions from the acquisition unit 33. Then, the execution unit 32 performs the virtual grid process on the basis of the scattered radiation transmittance Ts, the primary radiation transmittance Tp, and the imaging conditions, using Expressions (1) to (5).

Then, in Step S116, the execution unit 32 displays a radiographic image, from which the influence of scattered radiation has been removed by the virtual grid process, on the display unit 36 and ends the process.

After Step S104 or before a radiographic image is captured after Step S106, the user may finely adjust the imaging conditions. For example, in a case in which the physique of the subject 19 is normal and the thickness of the part to be imaged is slightly larger than that of a normal body type, the user may determine whether to adjust the imaging conditions such as the tube voltage. When the imaging conditions are adjusted, the derivation unit 28 may acquire an adjustment instruction, which is input by the user through the input unit 34, through the receiving unit 26 and instruct the radiation source control unit 22 to adjust the set imaging conditions on the basis of the acquired adjustment instruction. In a case in which the imaging conditions are adjusted in this way, the execution unit 32 performs the virtual grid process on the basis of the adjusted imaging conditions in Step S114.

Second Embodiment

Next, a second embodiment will be described. The same components as those in the radiography apparatus 10 according to the first embodiment are denoted by the same reference numerals and the detailed description thereof will not be repeated.

Since the structure of a radiography apparatus 10 is the same as that in the first embodiment (see FIG. 1), the description thereof will not be repeated. A derivation unit 28 according to this embodiment differs from the derivation unit 28 according to the first embodiment in that it estimates the body thickness (body thickness distribution) of the subject 19 on the basis of the radiographic image captured by the radiation detector 20 and derives virtual grid characteristics on the basis of the estimated value of the body thickness and the actual values of the imaging conditions acquired by the acquisition unit 33.

The estimation of the body thickness of the subject 19 by the derivation unit 28 according to this embodiment will be described. The derivation unit 28 combines an estimated primary radiation image Ip and an estimated scattered radiation image Is to generate an estimated image Im which is an image estimated to be obtained in a case in which a radiographic image of a virtual model M is captured. Then, the body thickness distribution of the virtual model M is corrected in order to reduce the difference between the estimated image Im and a radiographic image Ik of the subject 19 and a body thickness distribution $T_n$ is accurately corrected on the basis of the difference between the estimated image Im and the radiographic image Ik of the subject 19 so that the estimated image Im is close to the radiographic image Ik of the subject 19. The corrected body thickness distribution $T_n$ of the virtual model M is used as the body thickness distribution Tk of the subject K to determine a body thickness distribution Tk of the radiographic image Ik of the subject 19.

Specifically, the derivation unit 28 estimates the body thickness of the subject 19 as follows.

A table indicating the correspondence relationship between a density value (pixel value) and a body thickness is created for each of plural imaging conditions in advance and is stored in the storage unit 30. In addition, the storage unit 30 stores the virtual model M of the subject 19 having an initial body thickness distribution $T_0(x, y)$. It is assumed that various parameters required for each process and the generated images (for example, an estimated primary radiation image and an estimated scattered radiation image) are appropriately stored in the storage unit 30. The body thickness estimated by the derivation unit 28 means the sum of the thicknesses of the regions of the subject except for an air region on the path of the emitted radiation X.

First, the radiographic image Ik of the subject 19 is acquired from the radiation detector 20 through the derivation unit 28, the storage unit 30, and the detector control unit 24.

Then, the derivation unit 28 acquires the virtual model M having the initial body thickness distribution $T_0(x, y)$ from the storage unit 30. The virtual model M is data which virtually indicates the subject 19 and in which a body thickness that follows the initial body thickness distribution $T_0(x, y)$ is associated with each position on an x-y plane. In addition, characteristic information indicating, for example, structures (here, anatomic structures such as a lung field, a bone, and an organ) included in the virtual model M, the arrangement of the structures, and the characteristics of the structures with respect to radiation are set on the basis of the arrangement and composition of anatomic structures, such as the lung field, bones, and organs of the chest and abdomen of a comparative subject.

The virtual model M may have any initial body thickness distribution $T_0(x, y)$. However, in this embodiment, the initial body thickness distribution $T_0$ is generated and acquired as follows. The derivation unit 28 acquires the imaging conditions and acquires a table indicating the correspondence relationship between the pixel value corresponding to the imaging conditions of the subject 19 and the body thickness from the storage unit 30. Then, the derivation unit 28 acquires image data obtained by irradiating a comparative subject (human body) with the radiation X from the storage unit 30 and specifies the body thickness corresponding to the value of each pixel in the image data of the comparative subject on the basis of the table indicating the correspondence relationship to acquire the body thickness distribution of the image data of the comparative subject. Then, the derivation unit 28 acquires the body thickness distribution of the image data as the initial body thickness distribution $T_0$ (predetermined body thickness distribution) of the virtual model M as shown in the following Expression (6). The initial body thickness distribution $T_0$ may be generated during the process of acquiring the virtual model M as in this embodiment, or may be set before the process of acquiring the virtual model M in advance.

$$T_0(x, y) = \text{LUT}(I_k(x, y)) \tag{6}$$

Then, the derivation unit 28 combines the estimated primary radiation image Ip, which is obtained in a case in which the image of the virtual model M is captured under the same imaging conditions as the radiographic image of the subject 19, and the estimated scattered radiation image Is, which is obtained in a case in which the image of the virtual model M is captured under the same imaging conditions as the radiographic image of the subject 19, to generate the estimated image Im.

The derivation unit 28 generates the estimated primary radiation image Ip, which is obtained in a case in which the image of the virtual model M is captured under the same imaging conditions as the radiographic image of the subject 19, according to the following Expression (7), and generates the estimated scattered radiation image Is using the generated estimated primary radiation image Ip, according to the following Expression (8). Then, the derivation unit 28 combines the estimated primary radiation image Ip and the estimated scattered radiation image Is to generate the estimated image Im, as shown in the following Expression (9). When the estimated primary radiation image Ip and the estimated scattered radiation image Is are created first, the initial body thickness distribution $T_0(x, y)$ is used in the following Expressions (7) and (8). In this case, n is 1 in the following Expressions (7) and (8).

$$I_p(x, y) = I_o(x, y) \times \exp(-T_{n-1}(x, y) \times \mu) \tag{7}$$

$$I_s(x, y) = \sum_{x', y'} I_p(x', y') K_s(x, y, T_{n-1}(x', y'), \theta_{x', y'}) \tag{8}$$

$$I_m(x, y) = I_p(x, y) + I_s(x, y) \tag{9}$$

In the following Expression (7) and (8), (x, y) is the coordinates of a pixel position in the radiographic image of the subject 19. Ip(x, y) is an estimated primary radiation image at the pixel position (x, y). Is(x, y) is an estimated scattered radiation image at the pixel position (x, y). Io(x, y) is a dose at the pixel position (x, y). Im(x, y) is an estimated image at the pixel position (x, y). In addition, μ is a linear attenuation coefficient of the subject. $K_s(x, y, T_n(x', y'), \theta_{x', y'})$ is a convolution kernel indicating a point spread function corresponding to the body thickness of the subject at the pixel position (x, y). The dose Io(x, y) is a radiation dose which is detected by the radiation detector 20 on the assumption that the subject 19 is absent and varies depending on the imaging conditions. In addition, $\theta_{x', y'}$ indicates a parameter which is specified by the imaging conditions or the characteristic information of the virtual model M.

In addition, the estimated image Im may be an image which is estimated to be obtained in a case in which the virtual model M is irradiated with the radiation X and may be any image which is substantially regarded as a composite image of the estimated primary radiation image Ip and the estimated scattered radiation image Is. For example, the estimated image Im may be generated by the convolution integral of the kernel combining a primary radiation component and a scattered radiation component, using the following Expression (10), instead of Expressions (7) to (9). Here, $K_{p+s}(x, y, T_{n-1}(x', y'), \theta_{x', y'})$ is a kernel indicating a point spread function that combines the primary radiation component and the scattered radiation component. In addition, any model function may be used as long as it can generate an estimated image obtained by combining the estimated primary radiation image and the estimated scattered radiation image from the captured radiographic image.

$$I_m(x, y) = \sum_{x', y'} K_{p+s}(x, y, T_{n-1}(x', y'), \theta_{x', y'}) \tag{10}$$

Then, in a case in which the difference (error value $V_{error}$) between the radiographic image Ik of the subject 19 and the estimated image Im is small enough to be allowable, the derivation unit 28 determines the body thickness distribution $T_n$ as the body thickness distribution Tk of the radiographic image Ik of the subject 19.

In a case in which the error value $V_{error}$ is not small enough to be allowable, the derivation unit 28 corrects the body thickness distribution $T_{n-1}$ (the initial body thickness distribution $T_0$ in a case in which n is 1). The correction method is not particularly limited. Any correction method can be applied as long as it can acquire the correction value of each position in the body thickness distribution $T_{n-1}$ in order to reduce the difference between the radiographic image Ik of the subject 19 and the estimated image Im. For example, a process is performed which changes the body thickness distribution $T_{n-1}$ of the virtual model M for each partial region including one or more pixels in the virtual model M to calculate the body thickness of the partial region where the difference between the radiographic image Ik of the subject 19 and the estimated image Im is small. Then, the body thickness distribution of the virtual model M may be corrected using the calculated body thickness of each partial region.

In this way, the derivation unit 28 according to this embodiment can acquire the body thickness of the subject 19 on the basis of the radiographic image acquired from the radiation detector 20 through the detector control unit 24. A method for acquiring the body thickness of the subject 19 is not limited to the above-mentioned method. For example, as described in the execution unit 32 according to the first embodiment, the body thickness distribution T(x, y) of the subject 19 may be calculated by converting the pixel value of the radiographic image into a thickness, using a linear attenuation coefficient, on the assumption that the brightness distribution of the radiographic image is substantially identical to the body thickness distribution of the subject 19. Alternatively, the body thickness of the subject 19 may be measured using, for example, a sensor or may be approximated by a model, such as a cube or an elliptic cylinder.

Figure 4:
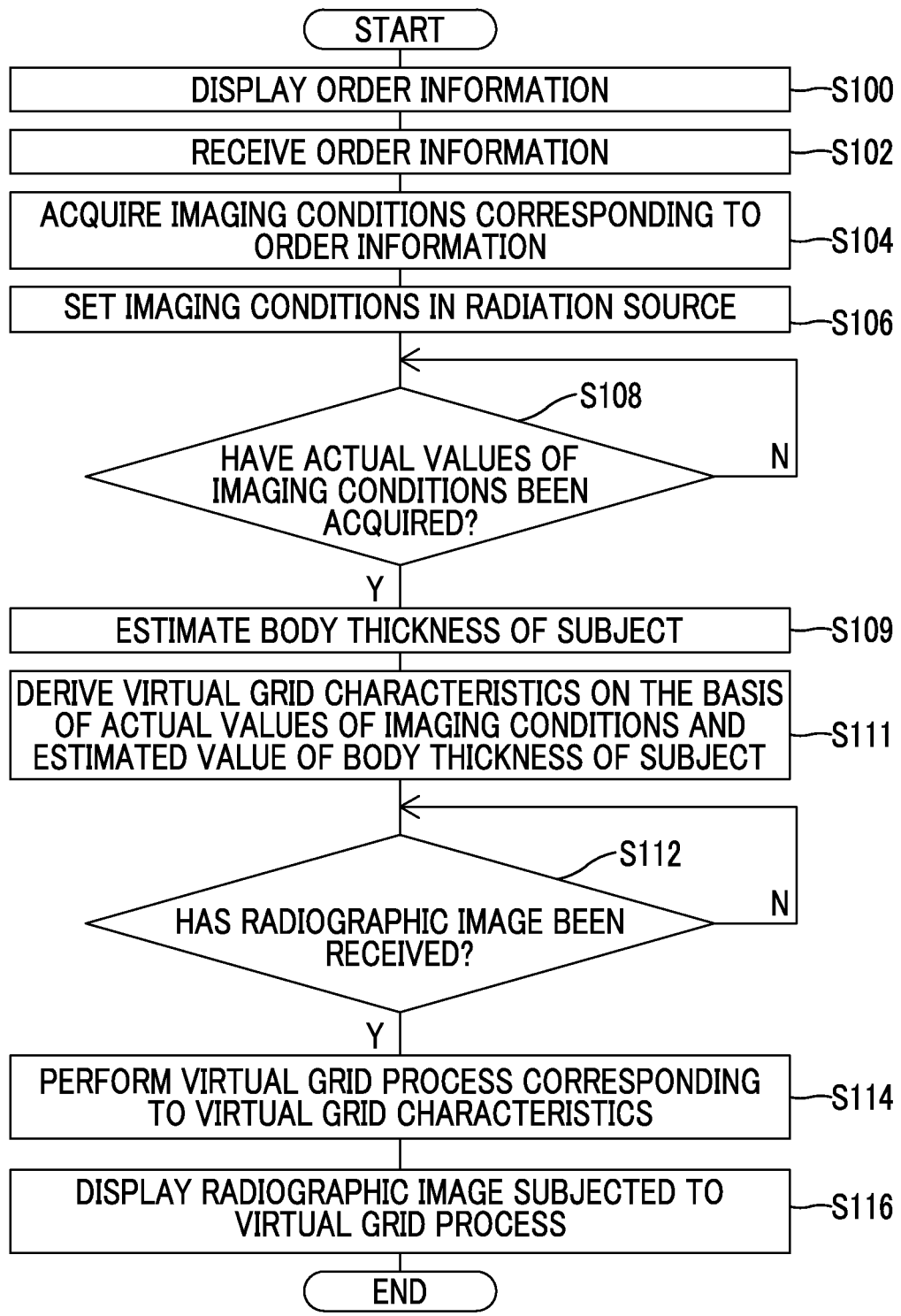
FIG. 4 is a flowchart illustrating an example of an imaging control process according to a second embodiment.

Next, the imaging control process according to this embodiment will be described. FIG. 4 is a flowchart illustrating an example of the imaging control process according to this embodiment. The imaging control process according to this embodiment differs from the imaging control process (see FIG. 3) according to the first embodiment in that it includes Step S111 instead of Step S110. Step S109 is provided between Step S108 and Step S111. The other steps in the imaging control process are the same as those in the first embodiment.

First, in Steps S100 to S108, the receiving unit 26 displays order information related to the capture of a radiographic image on the display unit 36. The user sets the radiation detector 20 and the radiation source 18 at an imaging position, with the subject 19 interposed therebetween, on the basis of the displayed order information. In addition, the user inputs the order information on the basis of the displayed order information. Then, the receiving unit 26 receives the order information input by the user. Then, the derivation unit 28 acquires the imaging conditions corresponding to the received order information on the basis of the table stored in the storage unit 30. Then, the derivation unit 28 sets the acquired imaging conditions in the radiation source control unit 22 of the control device 14. The radiation source control unit 22 controls the radiation source 18 on the basis of the imaging conditions set by the derivation unit 28 such that a radiographic image is captured. The detector control unit 24 controls the radiation detector 20 such that the radiation detector 20 detects the radiation X transmitted through the subject 19 and outputs a radiographic image indicating an image of the subject 19 to the detector control unit 24. The execution unit 32 determines whether a radiographic image has been received. In a case in which the execution unit 32 has received the radiographic image, the process proceeds to Step S109 after Step S108.

In Step S109, the derivation unit 28 estimates the body thickness of the subject 19 from the radiographic image of the subject 19, as described above.

Then, in Step S111, the derivation unit 28 derives the virtual grid characteristics (grid ratio) corresponding to the actual values of the imaging conditions acquired by the acquisition unit 33 and the estimated value of the body thickness of the subject 19 obtained in Step S109 on the basis of the table stored in the storage unit 30.

Each process in Steps S112 to S116 is the same as each process in Steps S112 to S116 (see FIG. 3) of the imaging control process according to the first embodiment. That is, in a case in which the execution unit 32 receives the radiographic image from the radiation detector 20 through the detector control unit 24, the execution unit 32 performs the virtual grid process, which corresponds to the virtual grid characteristics derived by the derivation unit 28 in Step S111, for the received radiographic image to remove the influence of scattered radiation from the radiographic image. Specifically, the execution unit 32 acquires the scattered radiation transmittance Ts and the primary radiation transmittance Tp corresponding to the derived virtual grid characteristics (grid ratio) from the table indicating the correspondence relationship which is stored in the storage unit 30. In addition, the execution unit 32 acquires the actual values of the imaging conditions from the acquisition unit 33. Then, the execution unit 32 performs the virtual grid process on the basis of the scattered radiation transmittance Ts, the primary radiation transmittance Tp, and the imaging conditions, using Expressions (1) to (5). In a case in which the virtual grid process is performed, the execution unit 32 according to this embodiment uses the estimated value which is estimated by the derivation unit 28 in Step S109 as the body thickness of the subject 19. The execution unit 32 displays the radiographic image, from which the influence of scattered radiation has been removed by the virtual grid process, on the display unit 36 and ends the process.

As such, in the radiography apparatus 10 according to this embodiment, the derivation unit 28 estimates the body thickness of the subject 19 and derives the virtual grid characteristics (grid ratio) on the basis of the estimated body thickness. Therefore, it is possible to derive appropriate virtual grid characteristics (grid ratio). In addition, the execution unit 32 can perform the virtual grid process, using the body thickness of the subject 19 estimated by the derivation unit 28. Therefore, it is possible to reduce the processing load of the execution unit 32.

Third Embodiment

Next, a third embodiment will be described. The same components as those in the radiography apparatus 10 according to each of the above-described embodiments are denoted by the same reference numerals and the detailed description thereof will not be repeated.

Since the structure of a radiography apparatus 10 is the same as that in each of the above-described embodiments (see FIG. 1), the description thereof will not be repeated. An imaging control process of the radiography apparatus 10 according to this embodiment includes processes different from those in the imaging control process according to the second embodiment (see FIG. 4) and different processes will be described.

Figure 5:
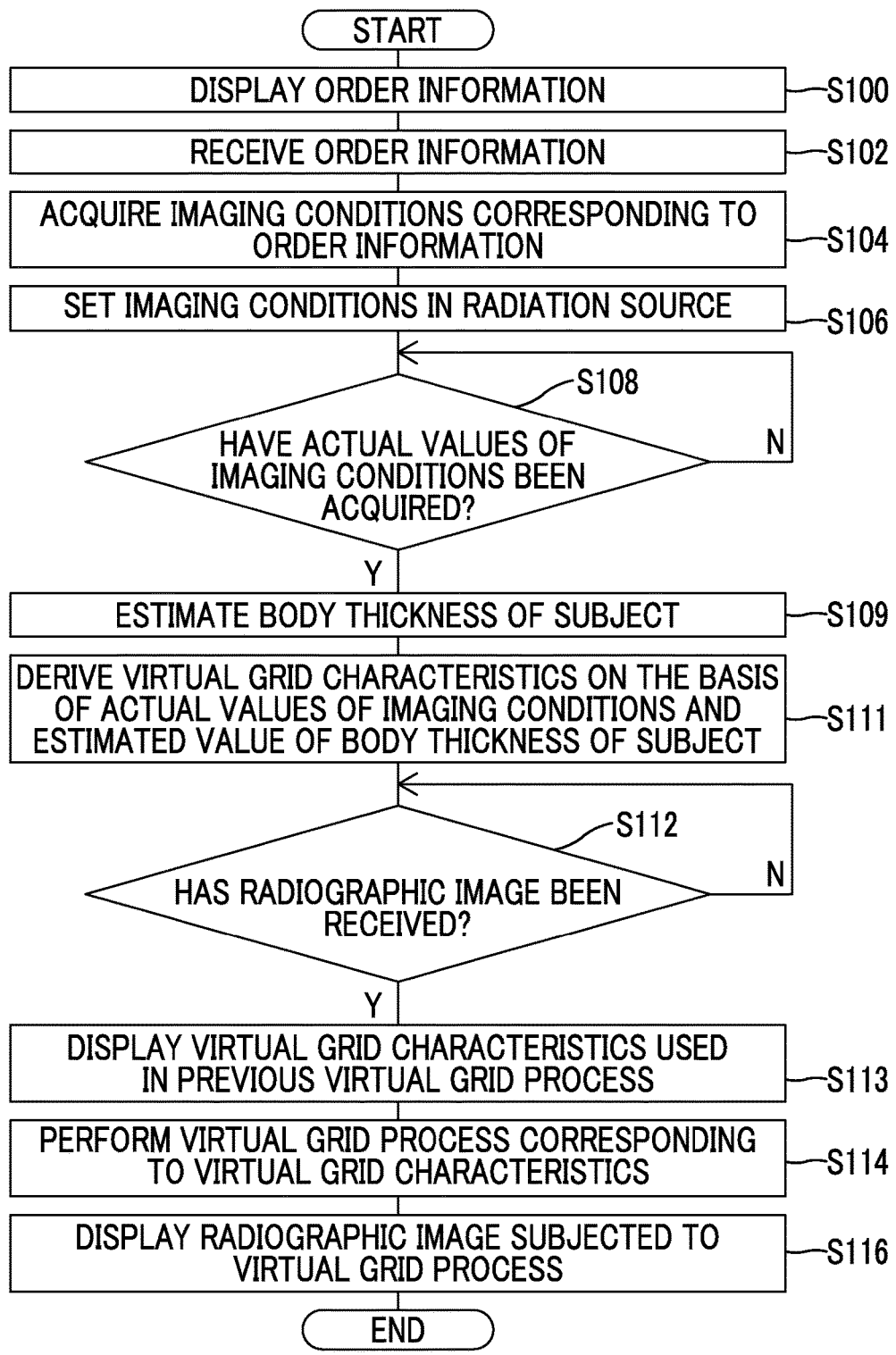
FIG. 5 is a flowchart illustrating an example of an imaging control process according to a third embodiment.

FIG. 5 is a flowchart illustrating an example of the imaging control process according to this embodiment. The imaging control process according to this embodiment differs from the imaging control process according to the second embodiment in that Step S113 is provided between Step S112 and Step S114 in the imaging control process according to the second embodiment. Therefore, as illustrated in FIG. 5, each process in Steps S100 to S112, S114, and S116 of the imaging control process according to this embodiment is the same as each process in Steps S100 to S112, S114, and S116 of the imaging control process according to the second embodiment. Here, a process in Step S113 of the imaging control process of the radiography apparatus 10 according to this embodiment will be described.

In Step S113 after Step S112 in which the execution unit 32 acquires the radiographic image from the radiation detector 20 through the detector control unit 24, the execution unit 32 displays the virtual grid characteristics used in the previous virtual grid process on the display unit 36. For example, in some cases, the user wants to perform the same virtual grid process as the previous virtual grid process in order to match the image quality (appearance) of the captured radiographic image of the same subject 19. Therefore, the radiography apparatus 10 according to this embodiment acquires the virtual grid characteristics used in the previous virtual grid process performed for the radiographic image of the same subject 19 and displays the virtual grid characteristics on the display unit 36. For example, preferably, the previous virtual grid characteristics and the virtual grid characteristics which are currently derived are displayed side by side such that the user can recognize a change in the virtual grid characteristics from the previous virtual grid characteristics.

In a case in which the previous virtual grid characteristics are included in the order information in advance, the previous virtual grid characteristics may be acquired from the order information or may be stored in the radiography apparatus 10 (for example, the storage unit 30) so as to be associated with information (for example, ID) for identifying the subject 19. In addition, in a case in which the image of the subject 19 is captured first, this step may be omitted.

The virtual grid characteristics for different subjects 19 may be displayed on the display unit 36. For example, in a case in which different subjects 19 are compared with each other, a radiographic image may be captured and then the virtual grid characteristics used to generate a radiographic image from which the influence of scattered radiation has been removed by the execution unit 32 may be displayed.

In a case in which the user wants to use the previous virtual grid characteristics, the user who has checked the virtual grid characteristics displayed on the display unit 36 in Step S113 inputs an instruction to change the virtual grid characteristics through the input unit 34.

Then, the derivation unit 28 performs the virtual grid process corresponding to the virtual grid characteristics in Step S114, displays the radiographic image subjected to the virtual grid process on the display unit 36 in Step S116, and ends the process. In Step S114, in a case in which an instruction to change the virtual grid characteristics is input in Step S113, the derivation unit 28 performs the virtual grid process corresponding to the instructed virtual grid characteristics (previous virtual grid characteristics).

As such, the radiography apparatus 10 according to this embodiment displays the virtual grid characteristics used in the previous virtual grid process during the capture of a radiographic image on the display unit 36. Therefore, it is easy for the user to check the virtual grid characteristics. As a result, for example, it is easy to match the image qualities (appearances) of the radiographic images.

Fourth Embodiment

Next, a fourth embodiment will be described. In this embodiment, a case in which the invention is applied to a radiography apparatus that performs energy subtraction imaging will be described. The same components as those in the radiography apparatus 10 according to each of the above-described embodiments are denoted by the same reference numerals and the detailed description thereof will not be repeated.

The energy subtraction imaging is an imaging method that irradiates the same subject with radiations having different energy levels plural times, acquires plural (two) radiographic images, and performs a difference calculation process for two radiographic images to enhance one of an image portion corresponding to a soft tissue and an image portion corresponding to a hard tissue of, for example, a bony part in the radiographic images and to remove the other image part, thereby acquiring a difference image (hereinafter, referred to as an "energy subtraction image"). For example, when an energy subtraction image corresponding to a soft tissue of the chest is used, it is possible to see a lesion hidden by the ribs and to improve a diagnosis performance. Hereinafter, a process which performs the difference calculation process, using the correspondence between pixels of two radiographic images, to generate an energy subtraction image is referred to as an energy subtraction process.

In the radiography apparatus 10 according to this embodiment, radiations having different energy levels are emitted plural times. Therefore, when two radiographic images are captured, different tube voltages are applied to the radiation source 18 to emit the radiation X. Hereinafter, a radiographic image which is captured by applying a high tube voltage (high energy) to the radiation source 18 to emit the radiation X is referred to as a high-voltage image and a radiographic image which is captured by applying a low tube voltage (low energy) to the radiation source 18 to emit the radiation X is referred to as a low-voltage image.

Figure 6:
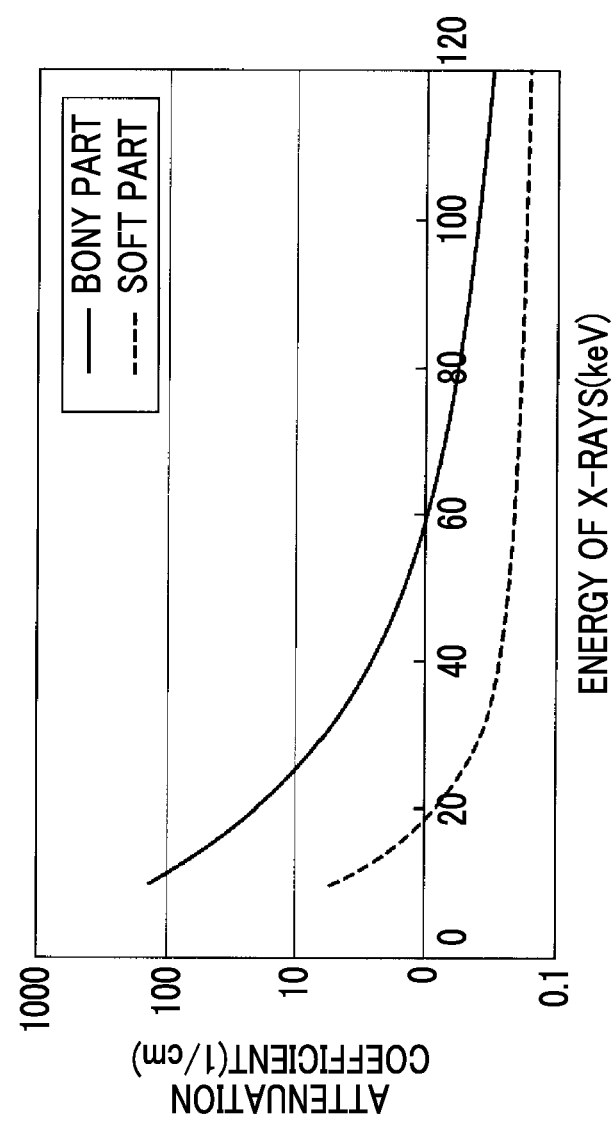
FIG. 6 is a diagram illustrating an example of a relationship between energy and scattered radiation.

FIG. 6 is a diagram illustrating an example of the relationship between the radiation attenuation coefficients of a bony part and a soft part of the human body and the tube voltage (energy) of the radiation source 18. As illustrated in FIG. 6, in the case of the low-voltage image in which the energy of the tube voltage is low, the difference between the radiation attenuation coefficients of the bony part and the soft part is large and the contrast between the two parts is high. On the other hand, in the case of the high-voltage image in which the energy of the tube voltage is high, the difference between the radiation attenuation coefficients of the bony part and the soft part is small and the contrast between the two parts is low. Therefore, in the energy subtraction process, the difference calculation process for calculating, for example, a low-voltage image−(a high-voltage image×a weighting coefficient) can be performed to generate an energy subtraction image for only a soft tissue.

Therefore, when an energy difference is increased during the capture of the high-voltage image and the low-voltage image and the energy subtraction process is performed, good energy separation occurs and an energy subtraction image with high contrast is obtained.

Figure 7:
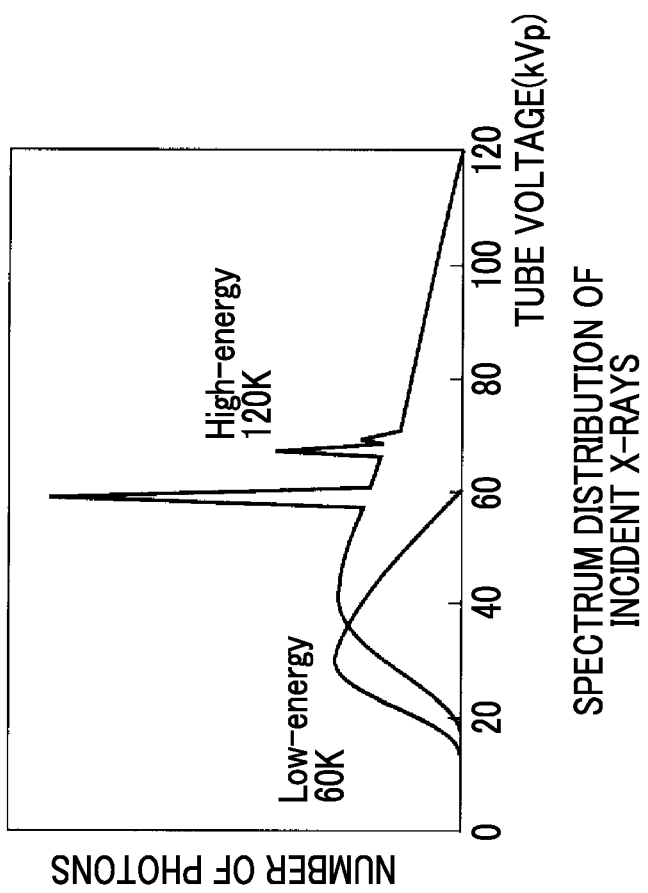
FIG. 7 is a diagram illustrating an example of a spectral distribution of two types of radiations X having different energy distributions.

FIG. 7 is a diagram illustrating an example of the spectral distribution of two types of radiation X having different energy distributions. In the example illustrated in FIG. 7, a case in which a tube voltage of 120 kVp is applied to emit high-energy radiation X and a case in which a tube voltage of 60 kVp is applied to emit low-energy radiation X are illustrated. As illustrated in FIG. 7, in a case in which a high tube voltage is applied to emit the radiation X, in practice, the emitted radiation X includes a low-energy component in addition to a high-energy component. Therefore, it is preferable to remove the low-energy component from the high-voltage image.

Figure 8:
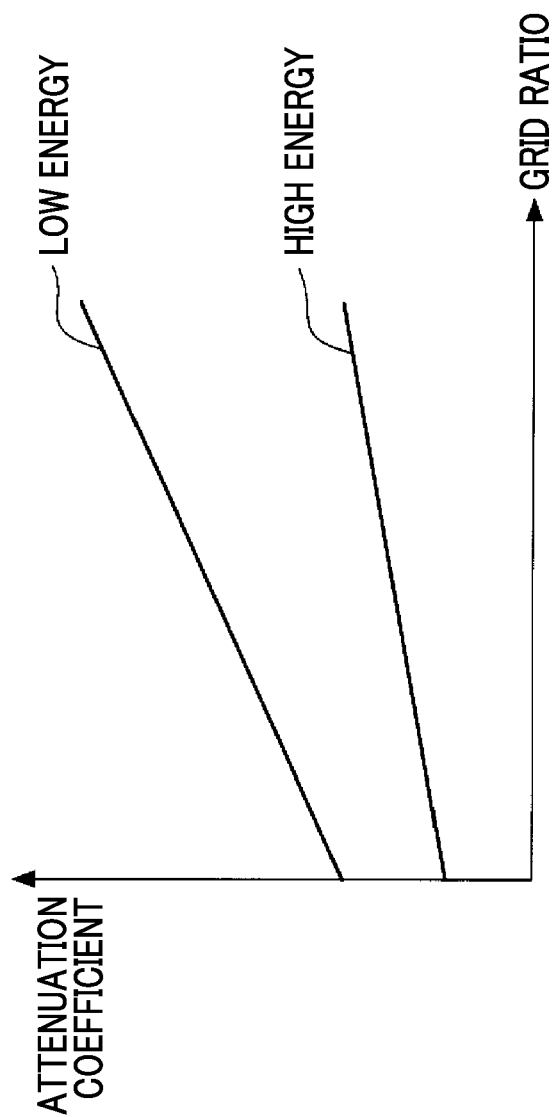
FIG. 8 is a diagram illustrating an example of a correspondence relationship between the grid ratio of high-energy radiation X and low-energy radiation X and an attenuation coefficient.

FIG. 8 is a diagram illustrating an example of the correspondence relationship between the grid ratio of the high-energy radiation X and the low-energy radiation X and an attenuation coefficient. As can be seen from FIG. 8, as the grid ratio becomes higher, the number of low-energy components removed is larger than the number of high-energy components removed.

As described above, as the energy of the radiation X increases, the amount of scattered radiation increases. Therefore, it is preferable that the grid ratio is high.

Therefore, it is preferable to perform the virtual grid process for the high-voltage image, using a high grid ratio, in order to remove the low-energy component and the scattered radiation. In addition, it is preferable to perform the virtual grid process for the low-voltage image, using a low grid ratio, in order to prevent a reduction in the pixel value obtained by an imaging process in which the amount of scattered radiation is small.

The radiography apparatus 10 according to this embodiment applies different tube voltages to capture the high-voltage image and the low-voltage image. Then, the virtual grid process is performed for the high-voltage image at a high grid ratio and is performed for the low-voltage image at a low grid ratio. The energy subtraction process is performed for the high-voltage image and the low-voltage image subjected to the virtual grid process to generate an energy subtraction image. For example, in a case in which the tube voltage is 40 kVp, a grid ratio of 3:1 is used. In a case in which the tube voltage is 100 kVp, a grid ratio of 10:1 is used.

Specifically, in the radiography apparatus 10 according to this embodiment, the execution unit 32 functions as an example of an energy subtraction processing unit and performs the energy subtraction process.

Figure 9:
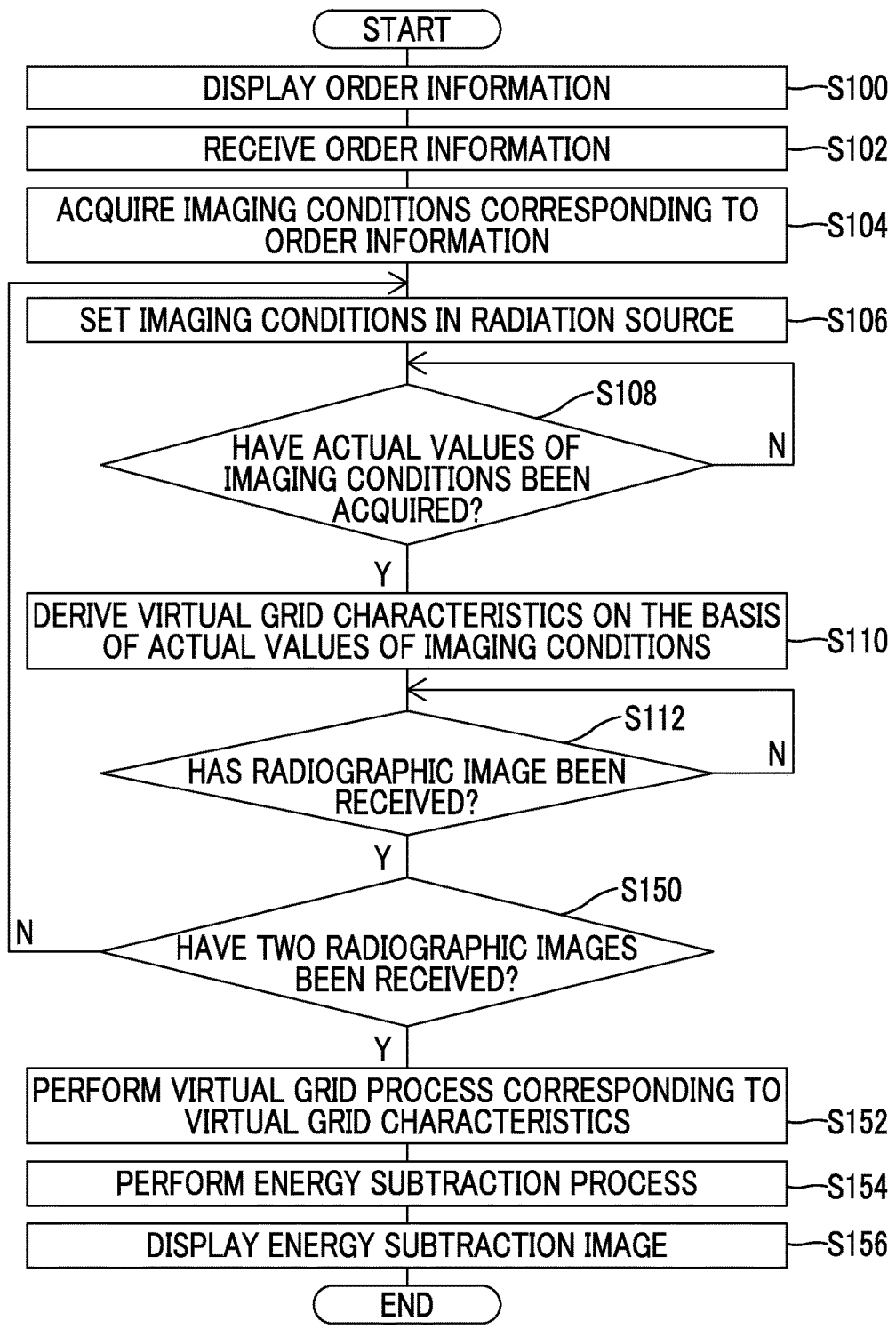
FIG. 9 is a flowchart illustrating an example of an imaging control process according to a fourth embodiment.

An imaging control process of the radiography apparatus 10 according to this embodiment in a case in which the energy subtraction imaging is performed will be described. FIG. 9 is a flowchart illustrating an example of the imaging control process according to this embodiment. The same steps as those in the imaging control process of the radiography apparatus 10 according to the first embodiment are denoted by the same reference numerals and the detailed description thereof will not be repeated.

In a case in which the energy subtraction imaging is performed, in the imaging control process illustrated in FIG. 9, the receiving unit 26 receives order information including information related to the energy subtraction imaging in Steps S100 to S150. Then, the radiography apparatus 10 captures two radiographic images (a high-voltage image and a low-voltage image) at different tube voltages of the radiation source 18 as the imaging conditions, on the basis of the received order information. The execution unit 32 receives the high-voltage image and the low-voltage image.

In a case in which the energy subtraction imaging is performed, two radiographic images (a high-voltage image and a low-voltage image) are required. Therefore, after Step S112, it is determined whether two radiographic images have been received in Step S150. In a case in which two radiographic images have not been received, the process returns to Step S106 and two radiographic images are captured.

When two radiographic images (a high-voltage image and a low-voltage image) are received, the process proceeds from Step S150 to Step S152 and the execution unit 32 performs the virtual grid process corresponding to the imaging conditions for each of the high-voltage image and the low-voltage image, similarly to Step S114 in the imaging control process according to the first embodiment. Then, in Step S154, the execution unit 32 performs the energy subtraction process for the high-voltage image and the low-voltage image subjected to the virtual grid process to generate an energy subtraction image. Then, in Step S156, the execution unit 32 displays the generated energy subtraction image on the display unit 36 and ends the process.

In the energy subtraction imaging of the radiography apparatus according to the related art, it is difficult to switch two types of grids with different grid ratios according to the high-voltage image and the low-voltage image due to problems, such as the body motion of the subject or costs. Therefore, in general, in a case in which the high-voltage image and the low-voltage image are captured, the high-voltage image and the low-voltage image are captured without using a grid or both the high-voltage image and the low-voltage image are captured using one type of grid.

In contrast, in the radiography apparatus 10 according to this embodiment, the derivation unit 28 derives the virtual grid characteristics of the high-voltage image and the low-voltage image on the basis of the actual values of the imaging conditions acquired by the acquisition unit 33. Therefore, it is possible to reduce the burden of an operation related to a change in the grid ratio on the user and to acquire an energy subtraction image in which good energy separation is achieved.

As described above, in the radiography apparatus 10 according to each of the above-described embodiments, the image processing device 12 includes the receiving unit 26, the derivation unit 28, the storage unit 30, the execution unit 32, and the acquisition unit 33. The receiving unit 26 receives the order information from the input unit 34. The derivation unit 28 acquires the imaging conditions corresponding to the received order information on the basis of the table stored in the storage unit 30 and sets the acquired imaging conditions in the radiation source control unit 22. The radiation source control unit 22 controls the radiation source 18 on the basis of the set imaging conditions such that a radiographic image is captured. The acquisition unit 33 acquires the actual values of the imaging conditions during imaging from the radiation source control unit 22. The derivation unit 28 derives the virtual grid characteristics on the basis of the actual values of the imaging conditions acquired by the acquisition unit 33. The execution unit 32 acquires the radiographic image captured by the radiation detector 20 through the detector control unit 24. The execution unit 32 performs the virtual grid process for the acquired radiographic image on the basis of the virtual grid characteristics derived by the derivation unit 28 and the imaging conditions acquired by the acquisition unit 33 to generate a radiographic image from which the influence of scattered radiation has been removed and displays the radiographic image on the display unit 36.

As such, in the radiography apparatus 10 according to each of the above-described embodiments, the derivation unit 28 derives the virtual grid characteristics on the basis of the actual values of the imaging conditions acquired by the acquisition unit 33. Therefore, when the user inputs the order information or the imaging conditions through the input unit 34, the execution unit 32 performs an appropriate virtual grid process. As a result, in the radiography apparatus 10 according to each of the above-described embodiments, it is possible to reduce the burden of an operation related to the setting of the imaging conditions on the user.

Figure 10:
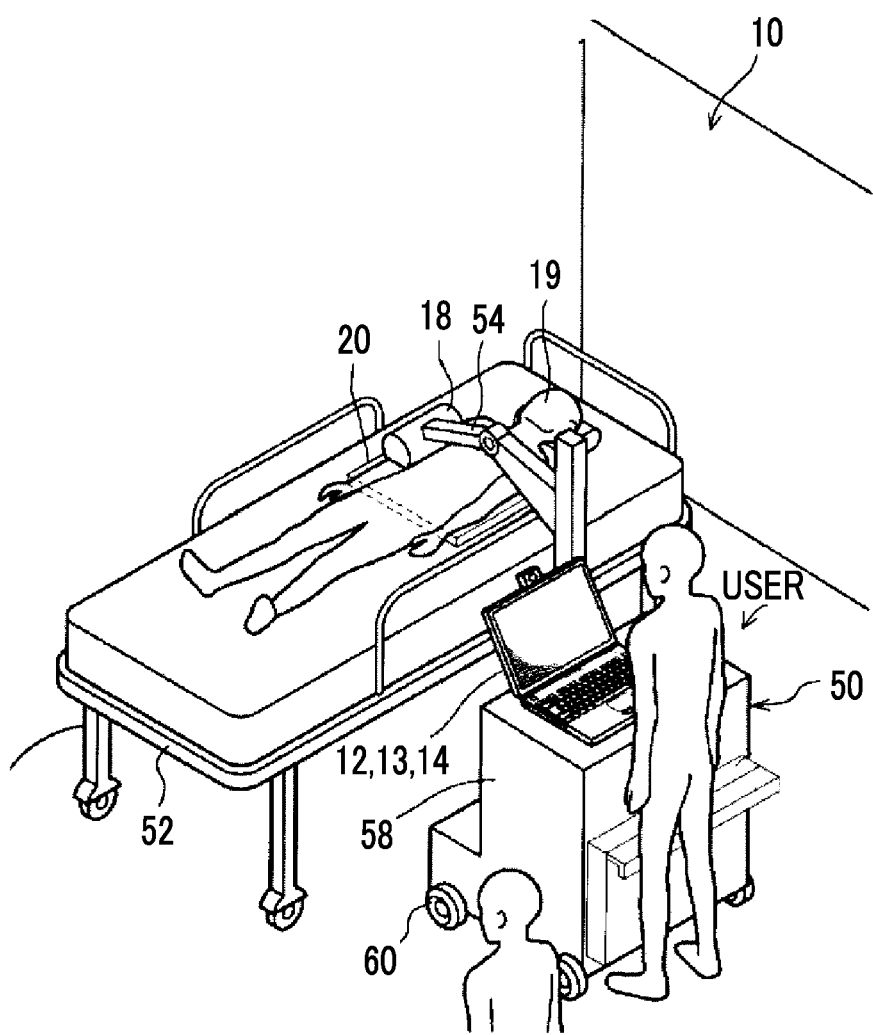
FIG. 10 is a diagram illustrating an example of a state in which the radiography apparatus according to each embodiment is applied to a medical cart and is arranged in a hospital room of a subject.

In the radiography apparatus 10 according to each of the above-described embodiments, the execution unit 32 acquires the radiographic image which has been captured, without actually providing a grid between the radiation detector 20 and the subject 19, and performs the virtual grid process as image processing for the acquired radiographic image to remove the influence of scattered radiation from the radiographic image. As described above, in the grid which is actually provided between the radiation detector 20 and the subject 19, interspace materials, such as lead and aluminum, are alternately arranged at a fine grid density. Therefore, the grid is weighty. For this reason, for example, as illustrated in FIG. 10 which will be described in detail below, the grid needs to be provided between the lying subject 19 and the radiation detector 20, which causes an increase in the burden of an arrangement operation and an increase in strain on the subject 19 during imaging. Further, in the case of a convergence-type grid, density unevenness is likely to occur in the radiographic image due to the oblique incidence of radiation. In addition, a subject image and a fine stripe pattern (moire) corresponding to the pitch of the grid are recorded on the radiographic image, which makes it difficult to see the radiographic image. For example, the technique disclosed in JP-A No. 2013-172881 has been known as image processing according to the related art which removes a stripe pattern. In the related art, in some cases, the processing time increases. In contrast, the radiography apparatus 10 according to each of the above-described embodiments performs the virtual grid process based on the virtual grid characteristics to remove the influence of scattered radiation from the radiographic image, without actually using a grid, similarly to the case in which a grid is provided. Therefore, it is possible to further reduce the burden of the subject 19 or the user. In addition, it is possible to prevent the problem that the radiographic image is difficult to see due to, for example, moire.

In the radiography apparatus 10, the execution unit 32 performs the virtual grid process on the basis of the virtual grid characteristics received by the receiving unit 26. Therefore, it is possible to instruct the virtual grid characteristics that are assumed to be used to control the amount of removal of scattered radiation.

In each of the above-described embodiments, the radiation detector 20 is an FPD. However, the invention is not limited thereto. The radiation detector may be other types. In addition, the structure of the radiography apparatus 10 is not particularly limited. It is preferable that the radiography apparatus 10 is applied to a medical cart. FIG. 10 illustrates an example of a state in which the radiography apparatus 10 is applied to a medical cart and is provided in a hospital room of the subject 19.

As illustrated in FIG. 10, the radiography apparatus 10 according to each of the above-described embodiments include the radiation detector 20 and a medical cart 50. The medical cart 50 includes the radiation source 18, the image processing device 12 that functions as a console, the U/I unit 13, and the control device 14. The radiation detector 20 is provided between a bed 52 and a patient as the subject 19 who lies on his or her back on the bed 52. The medical cart 50 according to each of the above-described embodiments include an arm 54 and the radiation source 18 is provided at one end of the arm 54. The radiation source 18 is provided above the subject 19 who lies on his or her back on the bed 52. In addition, the medical cart 50 includes wheels 60 that are provided at the bottom of a main body 58 and is movable in the hospital. When an instruction to capture a radiographic image is input through the U/I unit 13, the medical cart 50 captures a radiographic image on the basis of the imaging conditions, using the radiation detector 20, under the control of the image processing device 12 and the control device 14.

In each of the above-described embodiments, the derivation unit 28 derives the virtual grid characteristics on the basis of the actual values of the imaging conditions acquired by the acquisition unit 33. However, the invention is not limited thereto. For example, the derivation unit 28 may derive the virtual grid characteristics on the basis of the imaging conditions which are set in the radiation source control unit 22 by the derivation unit 28, such as the imaging conditions included in the order information or the imaging conditions instructed by the user.

In each of the above-described embodiments, radiation is not particularly limited. For example, X-rays or y-rays may be applied.

In addition, for example, the structure and operation of the radiography apparatus 10 according to each of the above-described embodiments are illustrative and can be changed according to the situation, without departing from the scope and spirit of the invention.

The entire disclosures of Japanese Patent Application No. 2014-070545 and Japanese Patent Application No. 2014-195704 are incorporated herein by reference.

All of the documents, the patent applications, and the technical standards mentioned in the specification are incorporated herein by reference to the same extent as that in a case in which the incorporation of the documents, the patent applications, and the technical standards by reference is specifically and individually mentioned.

What is claimed is:

1. A radiography apparatus that performs a scattered radiation removal process of removing an influence of scattered radiation included in radiation which has passed through a subject for a radiographic image captured by irradiating the subject with the radiation, comprising:

an acquisition unit that acquires imaging conditions of the radiographic image;

a derivation unit that derives virtual grid characteristics which are characteristics of a grid virtually used to remove the scattered radiation in the capture of the radiographic image and are used to set an amount of removal of the scattered radiation, on the basis of the imaging conditions acquired by the acquisition unit; and an execution unit that performs the scattered radiation removal process for the radiographic image with the amount of removal corresponding to the virtual grid characteristics derived by the derivation unit.

2. The radiography apparatus according to claim 1, further comprising:

a storage unit that stores the imaging conditions and the virtual grid characteristics corresponding to the imaging conditions so as to be associated with each other, wherein the derivation unit reads the virtual grid characteristics corresponding to the imaging conditions acquired by the acquisition unit from the storage unit and derives the virtual grid characteristics.

3. The radiography apparatus according to claim 1, wherein the derivation unit derives the virtual grid characteristics, using information related to a physique of the subject, in addition to the acquired imaging conditions.

4. The radiography apparatus according to claim 1, wherein the virtual grid characteristics are a grid ratio.

5. The radiography apparatus according to claim 1, wherein the acquisition unit acquires actual values of the imaging conditions.

6. The radiography apparatus according to claim 1, wherein the derivation unit derives the virtual grid characteristics on the basis of an estimated value of a body thickness of the subject.

7. The radiography apparatus according to claim 1, further comprising:
an energy subtraction processing unit,
wherein the radiography apparatus irradiates the subject with radiations having different energy levels to capture a first radiographic image and a second radiographic image,
the derivation unit derives virtual grid characteristics for each of the first radiographic image and the second radiographic image,
the execution unit performs the scattered radiation removal process for each of the first radiographic image and the second radiographic image, and
the energy subtraction processing unit matches pixels of the first radiographic image and the second radiographic image subjected to the scattered radiation removal process by the execution unit and performs a weighted difference calculation process to generate a difference image.

8. The radiography apparatus according to claim 7, wherein:
the virtual grid characteristics are a grid ratio; and
the grid ratio becomes higher as the energy level of the radiation emitted to the subject becomes higher.

9. A radiography method that performs a scattered radiation removal process of removing an influence of scattered radiation included in radiation which has passed through a subject for a radiographic image captured by irradiating the subject with the radiation, comprising:

acquiring imaging conditions of the radiographic image;
deriving virtual grid characteristics which are characteristics of a grid virtually used to remove the scattered radiation in the capture of the radiographic image and are used to set an amount of removal of the scattered radiation, on the basis of the acquired imaging conditions; and
performing the scattered radiation removal process for the radiographic image with the amount of removal corresponding to the derived virtual grid characteristics.

10. A non-transitory computer readable medium storing a radiography program that causes a computer to perform a radiography method which performs a scattered radiation removal process of removing an influence of scattered radiation included in radiation which has passed through a subject for a radiographic image captured by irradiating the subject with the radiation and to perform:
acquiring imaging conditions of the radiographic image;
deriving virtual grid characteristics which are characteristics of a grid virtually used to remove the scattered radiation in the capture of the radiographic image and are used to set an amount of removal of the scattered radiation, on the basis of the acquired imaging conditions; and
performing the scattered radiation removal process for the radiographic image with the amount of removal corresponding to the derived virtual grid characteristics.

* * * * *